United States Patent [19]

Forester et al.

[11] Patent Number: 5,160,331
[45] Date of Patent: Nov. 3, 1992

[54] ABSORBENT INSERT

[75] Inventors: Ralph H. Forester, Minneapolis; Arthur B. Finkelstein, Wayzata, both of Minn.

[73] Assignee: Progeny Products, Inc., St. Paul, Minn.

[21] Appl. No.: 801,695

[22] Filed: Dec. 2, 1991

Related U.S. Application Data

[63] Continuation-in-part of Ser. No. 730,261, Jul. 12, 1991.

[51] Int. Cl.$^5$ ............................................. A61F 13/15
[52] U.S. Cl. ............................ 604/364; 604/367; 604/368; 604/374
[58] Field of Search ............... 604/358, 364, 365, 367, 604/374, 393, 368; 428/283, 913, 171

[56] References Cited

U.S. PATENT DOCUMENTS

| | | | |
|---|---|---|---|
| 791,312 | 5/1905 | Bird et al. | 428/283 X |
| 2,600,576 | 6/1952 | Richard et al. | 604/374 X |
| 2,663,663 | 12/1953 | Weltman et al. | 154/121 |
| 3,665,923 | 5/1972 | Champaigne, Jr. | 604/365 X |
| 3,886,941 | 6/1975 | Duane et al. | 128/287 |
| 4,022,210 | 5/1977 | Glassman | 128/284 |
| 4,023,571 | 5/1977 | Comerford et al. | 128/290 |
| 4,036,234 | 7/1977 | Ishizuka | 128/287 |
| 4,055,180 | 10/1977 | Karami | 604/374 X |
| 4,072,150 | 2/1978 | Glassman | 128/284 |
| 4,081,301 | 3/1978 | Buell | 156/164 |
| 4,103,062 | 7/1978 | Aberson et al. | 604/374 X |
| 4,186,233 | 1/1980 | Krajewski et al. | 428/213 |
| 4,260,443 | 4/1981 | Lindsay et al. | 156/220 |
| 4,296,234 | 10/1981 | Mindt et al. | 536/47 |
| 4,352,356 | 10/1982 | Tong | 604/393 |
| 4,444,830 | 4/1984 | Erickson | 428/246 |
| 4,445,900 | 5/1984 | Roeder | 604/389 |
| 4,500,670 | 2/1985 | McKinley et al. | 524/445 |
| 4,556,441 | 12/1985 | Faase, Jr. | 156/247 |
| 4,574,024 | 3/1986 | VanMalderen | 156/202 |
| 4,585,685 | 4/1986 | Forry et al. | 428/283 X |
| 4,699,823 | 10/1987 | Kellenberger et al. | 604/368 X |
| 4,715,918 | 12/1987 | Lang | 156/273.1 |
| 4,815,963 | 3/1989 | Berkhout | 428/283 |
| 4,850,987 | 7/1989 | Gilomen | 604/393 X |
| 4,851,069 | 7/1989 | Packard et al. | 156/284 |
| 4,944,734 | 7/1990 | Wallach | 604/364 X |
| 4,985,023 | 1/1991 | Blank et al. | 604/358 X |
| 4,994,053 | 2/1991 | Lang | 604/367 |
| 5,021,050 | 6/1991 | Iskra | 604/379 |
| 5,083,650 | 1/1992 | Seiz et al. | 428/283 X |

Primary Examiner—Randall L. Green
Assistant Examiner—Mary Beth O. Jones
Attorney, Agent, or Firm—Kinney & Lange

[57] ABSTRACT

An environmentally sound absorbent insert for use with cloth diapers and the like. The insert comprises a sandwich of first and second webs constructed of non-toxic, biodegradable, pliable, liquid-absorbent material, such as tissue paper, with a layer of non-toxic, biodegradable, liquid-absorbent material sandwiched between them. The sandwich is bonded in an environmentally sound manner, such as by a mechanical bond (such as crimping) or by a non-toxic, biodegradable adhesive. The insert is used by placing it in the diaper so that the absorbent insert is sandwiched between layers of cloth. The cloth acts as a wick to draw fluids from the body of the wearer to the absorbent insert, to be retained until changing. One feature is a process for making the insert via a continuous feed process.

23 Claims, 4 Drawing Sheets

ABSORBENT INSERT

CROSS-REFERENCE TO RELATED APPLICATIONS

This application is a continuation-in-part of Ser. No. 07/730,261 filed Jul. 12, 1991.

BACKGROUND OF THE INVENTION

This invention relates to absorbent inserts, and particularly to absorbent inserts for use with diapers and the like.

Disposable diapers have become highly popular in the past several decades due to their superior ability to absorb and retain fluid. It is estimated that disposable diapers currently on the market are able to retain up to five times the amount of water as cloth or cotton diapers. However, there is a growing environmental concern that most disposable diapers are not fully biodegradable and/or recyclable.

A biodegradable material is one which, when disposed of, will not adversely pollute the land, water or air. Typically, the material will break down into constituents compatible with the environment. Many organic polymers are biodegradable; wood fiber products are both biodegradable and recyclable. Sewage treatment plants process biodegradable waste material by breaking them down and discharging the environmentally clean results into the environment. Non-biodegradable materials are incinerated into the air or disposed of at sea or in landfills, where they add to the environment problems. However, not all waste is directed to sewage treatment plants; some is disposed of directly at sea or into landfills, and other waste is recycled.

In the case of disposable diapers, it is common to employ a biodegradable absorbent material sandwiched between a liquid absorbent layer and a liquid impervious layer. Typically, flaps are employed which may secure parts of the diaper together for fastening to the body of the wearer. The flaps and liquid impervious layers are not biodegradable and will not disintegrate in hot or agitated water. Consequently, disposing of disposable diapers to the sewage system creates the risk of clogging drain pipes of the household. Therefore, users of disposable diapers seldom dispose of them to the sewage system, but instead dispose of them to the trash where they are added to the sea and landfill problems. Hence, the whole of the disposable diaper ends up in the solid waste disposal stream.

With growing environmental concerns, there has, in recent years, been a return to the use of cloth or cotton diapers. Cloth diapers may be laundered and reused and do not adversely impact the environment. As a result of the return to cloth diapers, there has been a resurgence of the diaper service industry which collects, launders and returns cloth diapers. However, as noted above, cloth diapers are only about one fifth as absorbent as disposable diapers. Consequently, there remains a substantial popularity for disposable diapers, even though they are not as environmentally sound as cloth diapers.

SUMMARY OF THE INVENTION

The present invention is directed to an absorbent insert for a diaper or the like which is environmentally sound, and may be used with cloth diapers. A cloth diaper with an insert according to the present invention is about on par with disposable diapers for liquid absorbency. In particular, a liquid absorbent insert according to the present invention comprises first and second webs constructed of nontoxic, biodegradable, pliable, liquid-absorbent material, such as tissue paper with a layer of nontoxic, biodegradable, liquid-absorbent material sandwiched between them. The structure is bonded together in an environmentally sound bond to form a fully biodegradable insert, the bond being a mechanical bond or a non-toxic, biodegradable adhesive. The liquid-absorbent material is preferably a powder or granular material and the tissue paper webs will disintegrate in hot water or on agitation. In a diaper, the insert is used by sandwiching it between layers of cloth. Upon soiling, the cloth diaper acts as a wick to draw fluids to the absorbent insert, to be retained there until the diaper is changed. The absorbent material absorbs a substantial amount of the fluid and urine from the wearer and the insert is disposed of by simply depositing it into the sewage system, such as by laundering it with the diaper in a washing machine. The hot water and agitation of the washing machine will disintegrate the tissue webs so that the paper and powder or granular absorbent material will easily pass through the waste pipes of the household.

In the preferred form of the invention, the granular absorbent material is sandwiched between the tissue webs by pressing the absorbent material into the web material so that the irregular granular shape of the absorbent material is impressed into the web material which conforms to retain the granules. Since common absorbent granules impress into both web tissues, the structure is held together by the granule/web interfaces.

In an alternative form of the invention, the web tissues are bonded together with a biodegradable adhesive.

One feature of the invention concerns the method of manufacturing the insert in a continuous process.

DETAILED DESCRIPTION OF THE PREFERRED EMBODIMENTS

Figure 1:
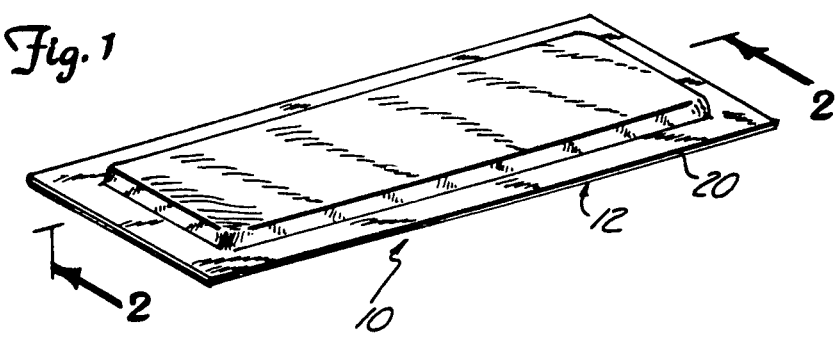
FIG. 1 is a perspective view of a diaper insert in accordance with one embodiment of the present invention.
Figure 2:
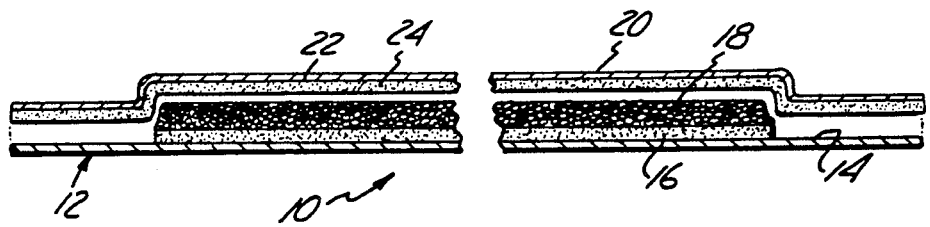
FIG. 2 is a section view taken along line 2—2 of FIG. 1.

FIGS. 1 and 2 illustrate a diaper insert in accordance with one embodiment of the present invention. Insert 10 comprises a first web 12 of non-toxic, biodegradable, pliable, liquid-absorbent material. Adhesive 16 is bonded to surface 14 at a central region of web 12 between the width and length of the web. The adhesive is a non-toxic, biodegradable adhesive which bonds on contact with slight pressure. A layer 18 of granular or powder non-toxic, biodegradable, liquid-absorbent material is bonded to the central region of web 12 by adhesive 16. A second web of non-toxic, biodegradable, pliable, liquid-absorbent material 20 has a layer of adhesive 22 bonded to its undersurface 24. Webs 12 and 20 are preferably non-toxic, biodegradable, pliable, liquid-absorbent cellulose tissue paper, such as No. 130-05 tissue paper available from Fort Howard Corporation of Green Bay, Wis. This paper is manufactured using 100% recycled paper and has a tensile strength of about 12.5 ounces per inch and a softness of not more than 14 grams. Absorbent layer 18 is preferably an absorbent polyacrylate polymer, one suitable such polymer being a cross-linked polymer, available from Dow Chemical Company of Midland, Mich. as DRYTECH 510. This material has an absorbent capacity of about 30 grams of urine per gram of material. This material is granular or powder in form with the grains of about 30% of the material (by weight) having a mesh size between 100 and 50, about 42% of the material (by weight) having a mesh size between 50 and 30, and about 20% of the material having a mesh size between about 30 and 20. The polymer is non-toxic and non-hygroscopic. Other suitable polymers include starch grafted polyacrylate polymers known as SANWETS from Hoechst-Celanese. The adhesive layers 16 and 22 are preferably a pressure sensitive adhesive which retains tackiness when wet but will disintegrate with sufficient agitation in hot water. The adhesive binds the absorbent powder and granular material to the tissues and the tissues to each other to hold the insert together. One suitable such adhesive is available from H. B. Fuller Company of St. Paul, Minn. (designated HL9415). As used herein, "hot" water normally has a temperature as found in households and typically is of the order of 120° to 140° F., above the warm temperature of body fluids of about 100° F.

Figure 3:
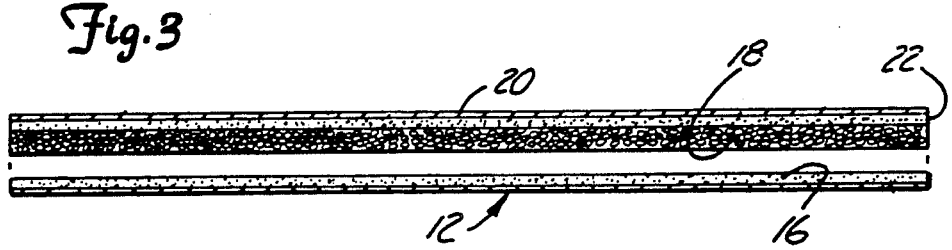
FIG. 3 is a section view of a modified diaper insert of the present invention.

FIG. 3 is a section view of a modification of the present invention wherein the insert is a laminate of tissues 12 and 20, adhesive layers 16 and 22, and absorbent material 18. The adhesive binds the absorbent material together and to tissues 12 and 20 to thereby hold the adhesive together. More particularly, as explained below the adhesive is applied under pressure to flow the adhesive into the absorbent powder and granules to bind the insert together without an edge as shown in FIG. 1.

For a diaper insert for use by an infant, the diaper insert is substantially rectangular, as shown in FIGS. 1-3 with dimensions of about 3 inches by 6 inches. For adult diapers, somewhat larger sizes are used.

Figure 4:
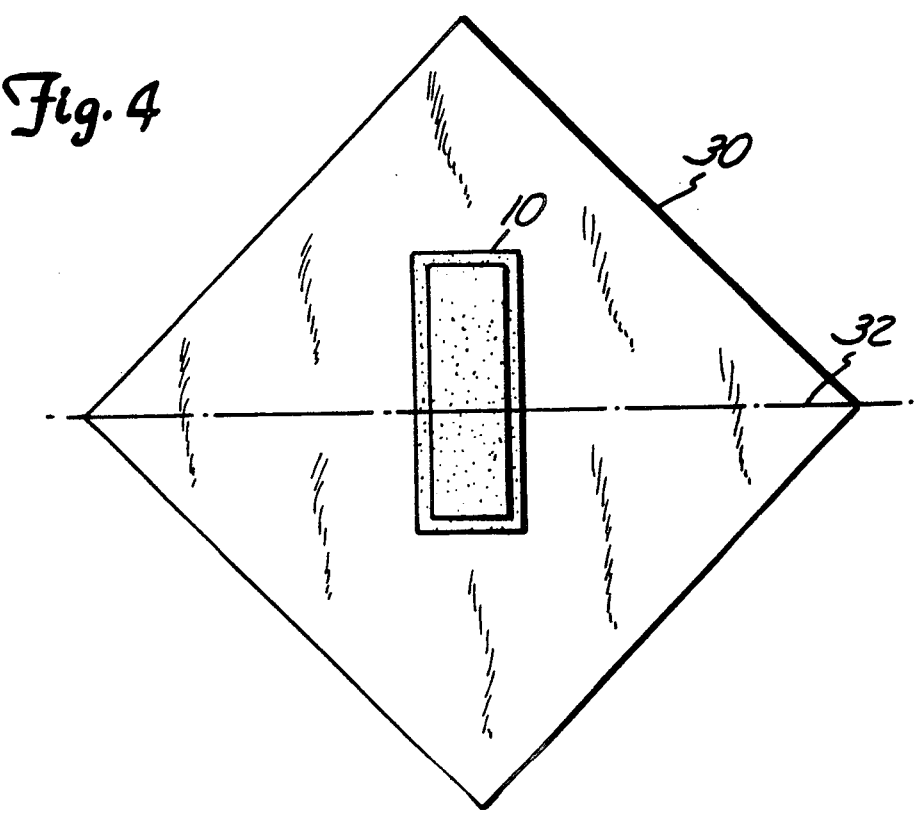
FIG. 4 is a plan view illustrating use of the insert in a standard cloth diaper.
Figure 5:
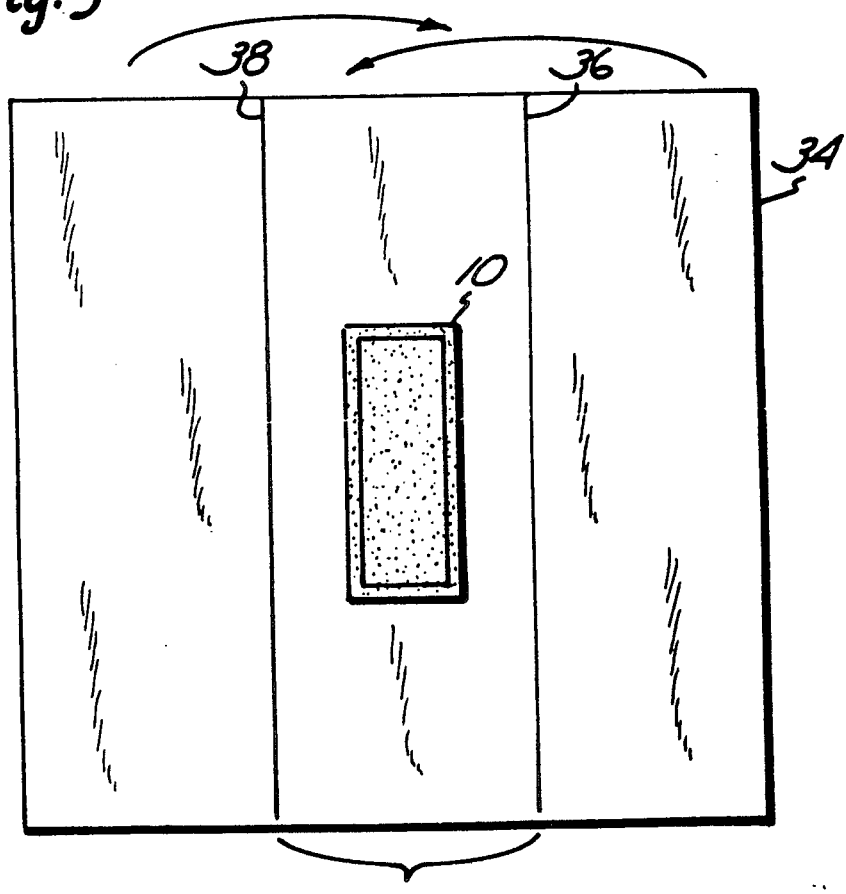
FIG. 5 is a plan view illustrating use of the insert in a prefolded cloth diaper.

Use of the diaper insert is illustrated in FIGS. 4 and 5; FIG. 4 being a conventional square cotton or cloth diaper and FIG. 5 being a prefolded cloth diaper. In the case of a square conventional diaper 30 shown in FIG. 4, insert 10 is placed in the approximate midpoint of the diaper and the diaper, and the insert, are folded along line 32 to the traditional triangular shape for wrapping about the body of the wearer. When so folded, the insert does not come in contact with the infant's skin. Likewise, in the case of a prefolded diaper as illustrated in FIG. 5, insert 10 is first placed in the central position as illustrated and the diaper is folded along lines 36 and 38 so that the sides are folded over the top of the central portion so that the insert again is not in contact with the infant's skin.

Upon soiling, the cloth diaper acts as a wick, drawing the liquids from the skin of the infant to the absorbent insert where the absorbent powder or granules swell to absorb and retain the liquid. When the diaper is changed, the cloth diaper may be rinsed in a toilet, whereupon the insert is flushed to the sewer system, or the diaper may be washed in a washing machine, whereupon the insert disintegrates and is discharged to the sewer system with the wash water. The sewage treatment plant break down the biodegradable granular or powder absorbent material and disintegrated adhesive and tissue. The broken down materials are then discharged to the environment, such as by incineration or discharging to land or sea. Hence, the biodegradable absorbent material, adhesive material and tissue are safely returned to the environment without adversely affecting the environment.

It is important that both webs 12 and 20 be constructed of liquid-absorbent material such as tissue paper. The reason for this is to permit absorption of liquids from the cloth diaper from both sides. Hence, as the cloth diaper acts as a wick to disperse the liquids, the dispersion will be directed to the inside and outside folds of the cloth. To assure absorption of fluids from both the inside and outside cloth layers, both webs 12 and 20 are liquid-absorbent.

Figure 6:
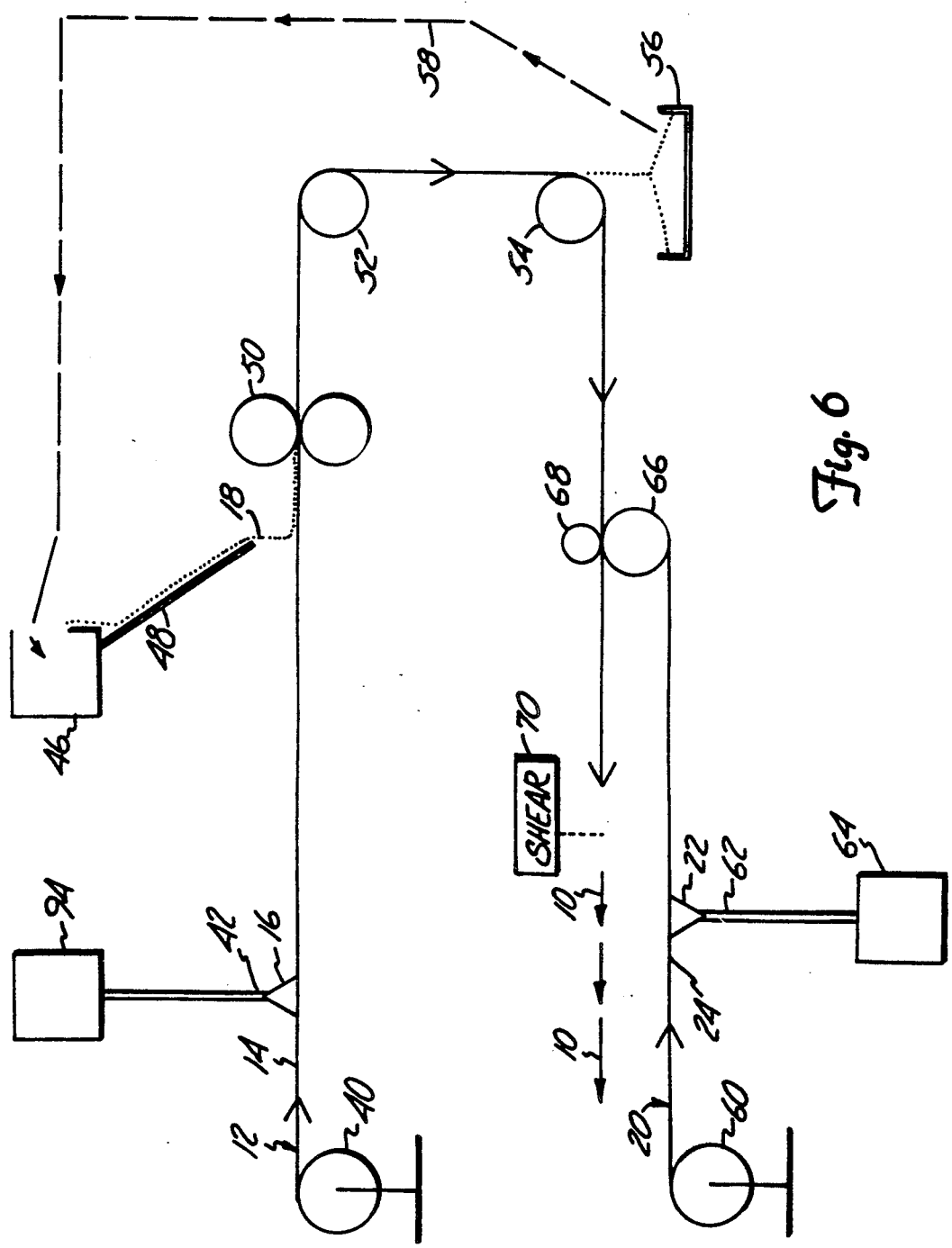
FIG. 6 is a schematic view illustrating one form of the process of manufacturing inserts in accordance with the present invention.

FIG. 6 illustrates one form of the process of manufacturing the inserts in accordance with the present invention. A continuous web 12 of tissue paper is payed off reel 40 and arranged to move horizontally. Adhesive is sprayed on upper surface 14 from discharge nozzle 42 and supply 44 in a hot melt process. Nozzle 42 is arranged to apply adhesive layer 16 to surface 14 of web 12 in selected successive central regions of the web. Thus, the edges of the eventual insert are not, at this time, coated with adhesive. Hence, the adhesive coating defines, for each insert, a central portion surrounded by an uncoated edge portion. The continuous web is fed past vibrator 46 containing a supply of powder or granular liquid-absorbent material, such as the DRYTECH or SANWET materials referred to above. The granular or powder absorbent material is vibrated from the supply by gravity down hopper 48 to pour onto the contact adhesive and upper surface of web 12. Pinch roller 50 presses the granular absorbent material to the adhesive to obtain a good bond thereof. Continued movement of continuous web 12 past rollers 52 and 54 turns web 12 and the liquid-absorbent material upside down so that excess liquid-absorbent granular or powder material is collected in bin 56 where it is recovered and returned to supply 46 as illustrated by dashed lines 58.

Meanwhile, continuous web 20 of tissue material is payed off reel 60 so that adhesive 22 is applied via nozzle 62 from supply 64. In this case, the entirety of surface 24 of web 20 is coated with adhesive. The direction of feeding of web 20 is reversed on roller 66 where it joins with web 12 bearing the absorbent material. Pinch roller 68 presses the assemblage together to thereby bond web 12 to web 20 to sandwich the absorbent material therebetween. The adhesive bonds the absorbent material to the tissues to form the pliant insert. The composite continuous web is then slit along the length of the web and sheared across the width at 70 in the edge regions between the successive central regions containing the granular or powder liquid-absorbent material. Hence, the separate inserts are formed.

Figure 7:
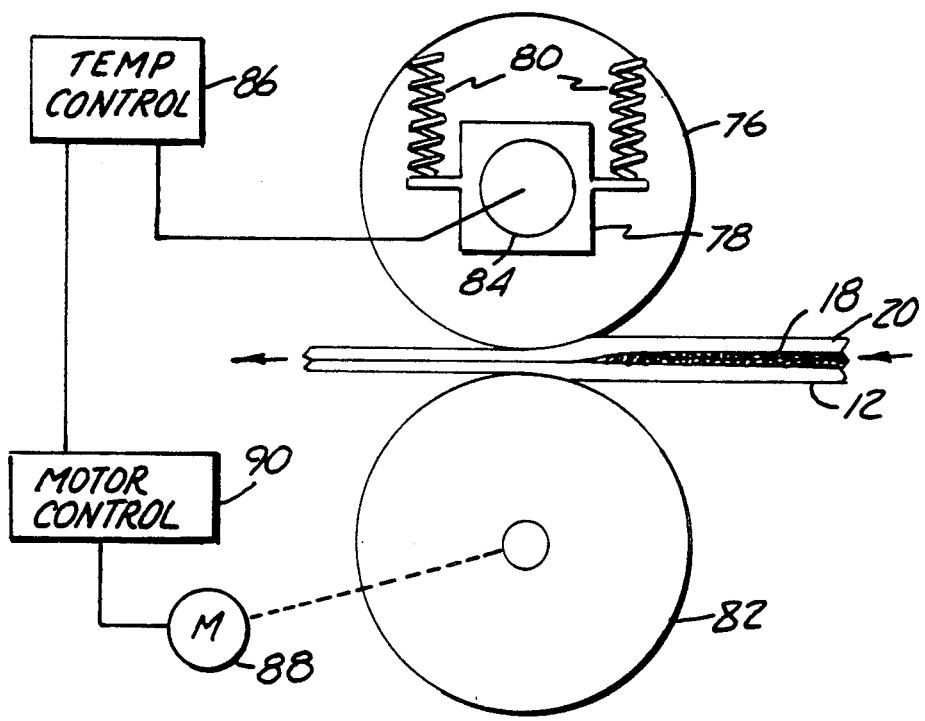
FIG. 7 is a schematic view illustrating a portion of the process of manufacturing inserts in accordance with the presently preferred embodiment of the present invention.
Figure 8:
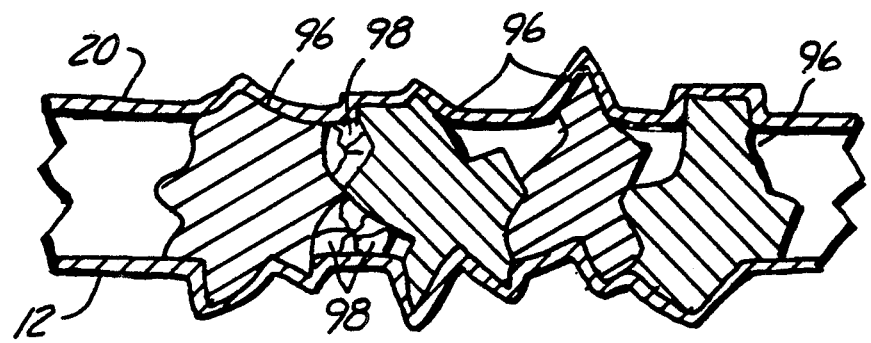
FIG. 8 is a section view of a portion of an absorbent insert in accordance with the presently preferred embodiment of the present invention.

FIG. 7 illustrates a preferred modification of the process illustrated in FIG. 6 to produce a preferred absorbent insert more fully described in conjunction with FIG. 8. More particularly, instead of applying an adhesive to bond the absorbent material 18 to webs 12 and 20, the sandwich is simply pressed together in a hot roller press to conform the web material to the granules of absorbent material to mechanically bond the sandwich. Thus, web 12 is payed off reel 40, and granular material 18 is vibrated onto surface 14 of web 12 as illustrated in FIG. 6. Supply 94 and nozzle 42 are eliminated so no adhesive is applied to web 12. Payoff reel 60 is arranged to supply web 20 directly over the top of absorbent material 18, without adhesive and without turning over the sandwich as shown in FIG. 6. The sandwich comprising webs 12 and 20 with absorbent material 18 therebetween is advanced through the hot pressure roller assembly shown in FIG. 7.

The roller assembly illustrated in FIG. 7 illustrates a hollow, heated pinch roller 76 journaled to housing 78 which is biased by controlled spring bias 80 to bias roller 76 toward drive roller 82. Heating bar or element 84 is carried by pinch roller 76, and is connected to an electronic temperature control 86. Conveniently, temperature sensors (not shown) may be included for sensing the temperature of roller 76 and to control temperature control 86. Drive roller 82 is connected to drive motor 88, which in turn is connected to electronic motor control 90. Motor control 90 may conveniently be connected to temperature control 86 to receive control signals from the temperature control.

Drive motor 86 drives drive roller 82 to provide the principal drive for the web materials. Pinch roller 76 is biased toward driver roller 82 to provide between about 5 and 40 pounds of pressure onto the sandwich consisting of webs 12 and 20 and absorbent material 18. In addition, heater 84 is controlled to heat pinch roller to a temperature of between about 200° and 400° F. The result of the heat and pressure causes the web material to deform to conform to the irregular shape of the individual grains of granular absorbent material. The conforming of the webs to the grains causes the grains to bond to both webs to thereby bond the sandwich together.

The foregoing ranges of temperature and pressure are, of course approximate, as the exact temperature and pressure used will depend on the thickness of the web material used and the speed of movement of the sandwich between the rollers. Suffice it to say, that higher pressures within the range of 5 to 40 pounds will permit lower temperatures. The pressure must not be so high as to substantially crush the granules of absorbent material, yet must be high enough to deform the web material to conform the web material to the irregular shape of the grains. The temperature must not be so high as to risk igniting the web material, yet should be high enough to impart resiliency to the web material to permit it to conform to the shape of the grains. The speed of transport of the sandwich between the rollers will also affect the temperature, as higher speeds permit higher roller temperatures (because the webs are not heated as high).

The mesh size of the absorbent material should be such that substantial portion of the grains are large enough to deform both webs 12 and 20, yet small enough that the webs conform to the irregular shape of the grains to form a mechanical bond to bond the sandwich together. Thus, a grain size smaller than about 100 mesh (0.010 inch) does not indent and conform to the tissue material of webs 12 and 20 to adequately bond the sandwich, whereas a grain size larger than about 10 mesh (0.100 inch) will cause some tearing of the tissue of the web material when pressed as described in connection with FIG. 7. We have found that the above-described DRYTECH 510 material, having a grain size predominantly between about 20–100 mesh, provides good mechanical bonding characteristics.

It is not necessary that webs 12 and 20 conform to all grains of absorbent material, nor is it necessary that all grains be larger than about 100 mesh. Smaller grains and powder may also be included in the layer of absorbent material, provided a sufficient quantity (preferably more than half by weight), be of good size for mechanical bonding. Thus, FIG. 8 illustrates a cross-section of a portion of an absorbent insert having webs 12 and 20 conformed to the irregular granular shape of grains 96 to thereby mechanically bond the sandwich together, whereas powder 98 is also dispersed in the absorbent layer. Since the mechanical bond formed by conforming the webs to the irregular shape of the grains, the bond is bio-degradable with the absorbent material and the web tissues.

Conveniently, the manufacturing process may be accomplished employing continuous webs of tissue paper of a convenient width, with the spray of adhesive from nozzle 42 being controlled to apply the adhesive layer 16 in patches approximately 5 inches wide by 2 inches long, separated by about an inch. When slit and sheared at 70, slitting may be done into six-inch strips along the length of the web (to define the length of the inserts), and shearing may be accomplished at about three-inch intervals, thereby defining the width of the ultimate inserts 10. Alternatively, the inserts may be slit to three-inch wide webs and sheared at six-inch intervals.

The present invention thus provides a liquid-absorbent insert for use with diapers and the like which will disintegrate, in a reasonable period of time, in a sanitary sewer system, or in a commercial or home washing machine. All of the materials forming the disposable insert are non-toxic and biodegradable. The materials are neither toxic to the biological system of the sewer treatment plant nor add toxicity to the sludge or to the environment however the materials are discharged. Hence, the insert according to the present invention presents no hazard to the environment, or to the sewer treatment plant.

While the insert has been described in connection with incontinency products, such as infant and adult diapers, it is useful in numerous environments where liquids are to be absorbed for retention and/or disposal. Thus, the insert is useful in bedpans to absorb liquid to facilitate removal of the bedpan, in portable toilets, in infant training toilets, as disposable mop heads, as disposable towels and mop rags, and the like. Also, it may be desirable for some uses to include an odor suppressant to remove odors or a perfume to mask odors associated with absorbed liquids.

Although the present invention has been described with reference to preferred embodiments, workers skilled in the art will recognize that changes may be made in form and detail without departing from the spirit and scope of the invention.

What is claimed is:

1. A biodegradable liquid-absorbent insert comprising:

first and second outer webs of non-toxic, biodegradable, pliable, liquid-absorbent material;

a liquid-absorbent layer comprising non-toxic, biodegradable, liquid-absorbent granules sandwiched between the first and second webs, at least some of the granules comprising irregularly-shaped grains, the first and second webs assuming the irregular shape of a substantial number of individual ones of the grains to mechanically bond the first and second webs together with the granules sandwiched between said assumed irregular shape.

2. The liquid-absorbent insert of claim 1 where the liquid-absorbent layer is mechanically bonded to the first and second webs by pressing the grains into the first and second webs.

3. The liquid-absorbent insert of claim 2 where the first and second webs assume to the shape of the grains by deforming the webs without perforation.

4. The liquid-absorbent insert of claim 1 where the first and second webs are cellulose fiber materials.

5. The liquid-absorbent insert of claim 1 where first and second webs are tissue paper.

6. The liquid-absorbent insert of claim 1 where the liquid-absorbent granules are a polyacrylate polymer.

7. The liquid-absorbent insert of claim 1 where the liquid-absorbent granules are selected from the group consisting of crosslinked polyacrylate polymer and starch-grafted polyacrylate polymer.

8. The liquid-absorbent insert of claim 1 where the first and second webs assume to the shape of the grains by deforming the webs without perforation.

9. The liquid-absorbent insert of claim 1 where at least one-half by weight of the granules comprises irregularly-shaped grains having a size between about 10 and 100 mesh.

10. The liquid-absorbent insert of claim 9 where the first and second webs assume to the shape of the grains by deforming the webs without perforation.

11. The liquid-absorbent insert of claim 9 where the liquid-absorbent layer is mechanically bonded to the first and second webs by pressing the grains into the first and second webs.

12. The liquid-absorbent insert of claim 11 where the first and second webs assume to the shape of the grains by deforming the webs without perforation.

13. The liquid-absorbent insert of claim 1 where the liquid-absorbent layer consists essentially of said liquid-absorbent granules.

14. The liquid-absorbent insert of claim 13 where the first and second webs assume to the shape of the grains by deforming the webs without perforation.

15. The liquid-absorbent insert of claim 13 where the liquid-absorbent layer is mechanically bonded to the first and second webs by pressing the grains into the first and second webs.

16. In a cotton diaper for fastening to the body of a wearer, the diaper having a crotch section, the improvement comprising a removable, disposable, biodegradable liquid-absorbent insert in the crotch section, the insert comprising:

first and second outer webs of non-toxic, biodegradable, pliable, liquid-absorbent material;

a liquid-absorbent layer comprising non-toxic, biodegradable, liquid-absorbent granules sandwiched between the first and second webs, at least some of the granules comprising irregularly-shaped grains, the first and second webs assuming the irregular shape of a substantial number of individual ones of the grains to mechanically bond the first and second webs together with the granules sandwiched between said assumed irregular shape.

17. The diaper of claim 16 where the liquid-absorbent layer is mechanically bonded to the first and second webs by pressing the grains into the first and second webs.

18. The diaper of claim 17 where at least one-half by weight of the granules comprises irregularly-shaped grains having a size between about 10 and 100 mesh.

19. The diaper of claim 17 where the first and second webs assume to the shape of the grains by deforming the webs without perforation.

20. The diaper of claim 16 where the diaper is folded to enclose the insert so the insert does not contact the wearer.

21. The diaper of claim 16 where at least one-half by weight of the granules comprises irregularly-shaped grains having a size between about 10 and 100 mesh.

22. The diaper of claim 16 where the first and second webs assume to the shape of the grains by deforming the webs without perforation.

23. The diaper of claim 16 where the liquid-absorbent layer consists essentially of said liquid-absorbent granules.

* * * * *

UNITED STATES PATENT AND TRADEMARK OFFICE
CERTIFICATE OF CORRECTION

PATENT NO. : 5,160,331
DATED : November 3, 1992
INVENTOR(S) : RALPH H. FORESTER, ARTHUR B. FINKELSTEIN It is certified that error appears in the above-identified patent and that said Letters Patent is hereby corrected as shown below:

Col. 7, line 11, delete "shape.", insert "shapes."

Col. 7, line 17, after "assume", delete "to"

Col. 7, line 30, after "assume", delete "to"

Col. 7, line 37, after "assume", delete "to"

Col. 7, line 44, after "assume", delete "to"

Col. 8, line 5, after "assume", delete "to"

Col. 8, line 26, delete "shape", insert "shapes"

Col. 8, line 35, after "assume", delete "to"

Col. 8, line 44, after "assume", delete "to"

Signed and Sealed this

Twelfth Day of October, 1993

Attest:

BRUCE LEHMAN

Attesting Officer     Commissioner of Patents and Trademarks